United States Patent [19]

Singh et al.

[11] Patent Number: 5,202,251

[45] Date of Patent: Apr. 13, 1993

[54] MONOCOT-SPECIFIC MONOCLONAL ANTIBODIES AGAINST ACETOHYDROXYACID SYNTHASE

[75] Inventors: Bijay K. Singh, Hamilton Square; Bosco S. Wang, Cranbury; Araceli L. Lumanglas, Jersey City, all of N.J.

[73] Assignee: American Cyanamid Company, Stamford, Conn.

[21] Appl. No.: 560,677

[22] Filed: Aug. 3, 1990

[51] Int. Cl.$^5$ .................. C12N 5/20; C12N 15/02; C07K 15/28; C12P 21/08
[52] U.S. Cl. .................. 435/240.27; 530/388.26; 435/70.21; 435/172.2
[58] Field of Search .................. 530/387, 388.26; 435/240.27, 172.2, 70.21

[56] References Cited
FOREIGN PATENT DOCUMENTS
0257993  2/1988  European Pat. Off. .

OTHER PUBLICATIONS

Mazur et al: Plant Physiol. 85: 1110–1117, 1985.
Durner et al. Z. Naturforsch 43:850–856, 1988.
Maurer et al. Mtds in Enzymology 70:49–70, 1988.
Lerner, Nature 299:592–596, 1982.

*Primary Examiner*—David L. Lacey
*Assistant Examiner*—Paula Hutzell
*Attorney, Agent, or Firm*—Alan M. Gordon

[57] ABSTRACT

This invention is directed to the generation of hybridomas and the monocot-specific monoclonal antibodies prepared from those hybridomas against the acetohydroxyacid synthase enzyme. The monoclonal antibodies are useful to isolate and purify the enzyme. The invention is also directed to peptides corresponding to fragments of the enzyme which then are used to generate the monoclonal antibodies.

3 Claims, 8 Drawing Sheets

FIG. 1

10
Glu Phe Arg Leu Thr Arg Ser Pro Val [X] Ala Asn His Leu Phe Arg His 20                            30
Glu Gln Gly Glu Ala Phe Ala Ala Ser Ala Tyr Ala Arg Ser Ser Gly Arg 40                         50
Val Gly Val Cys Ile Ala Thr Ser Gly Pro Gly Ala Thr Asn Leu Val Ser

60
Ala Leu Ala Asp Ala Leu Leu Asp Ser Val Pro Ile Val Ala Ile Thr Gly 70                         80
Gln Val Pro Arg Arg Met Ile Gly Thr Asp Ala Phe [X] Glu Thr Ala Ile 90                      100
Val Glu Val Thr Cys Ser Ile Thr Lys His Asn Tyr Leu Val Ser Ser Arg

110
Leu Thr [X] Pro Arg Val Val Gln Glu Ala Phe Phe Leu Ala Ser Ser Gly 120                            130
Arg Pro Gly Pro Val Leu Val Asp [X] Pro Lys Asp Ile Gln Gln Gln Met 140                        150
Ala Val Arg Ala Trp Asp Thr Pro Met Ser Leu Pro Gly Tyr Ile Ala Arg 160                       170
Leu Pro Lys Pro Pro Ala Thr Glu Phe Leu Glu Gln Val Leu Arg Leu Val

FIG. 1 (cont.)

```
                         180
Gly Glu Ser Thr Ala Pro Val Leu Tyr Val Gly Gly Gly Cys Ala Ala Ser
        190                                 200
Gly Glu Glu Leu Cys Arg Phe Val Glu Leu Thr Gly Ile Pro Val Thr Thr
                     210                                 220
Thr Leu Met Gly Leu Gly Asn Phe Pro Ser Asp Asp Pro Leu Ser Leu Arg
                             230
Met Leu Gly Met His Gly Thr Val Tyr Ala Asn Tyr Ala Val Asp Lys Ala
    240                                 250
Asp Leu Leu Leu Ala Phe Gly Val Arg Phe Asp Asp Arg Val Thr Gly Lys
                 260                             270
Ile Glu Ala Phe Ala Gly Arg Ala Lys Ile Val His Ile Asp Ile Asp Pro
                         280
Ala Glu Ile Gly Lys Asn Lys Gln Pro His Val Ser Ile Cys Ala Asp Val
290                                 300
Lys Leu Ala Leu Gln Gly Met [X] Thr Leu Leu Glu Gly Ser Thr Ser Lys
             310                                 320
Lys Ser Phe Asp Phe Gly Ser Trp His Asp Glu Leu Asp Gln Gln Lys Arg
                         330
Glu Phe Pro Leu Gly Tyr Lys Thr Ser Ile Gly Asn Pro Ala
```

MONOCOT-SPECIFIC MONOCLONAL ANTIBODIES AGAINST ACETOHYDROXYACID SYNTHASE

FIELD OF THE INVENTION

This invention relates to the generation of hybridomas and the monocot-specific monoclonal antibodies prepared from those hybridomas against the acetohydroxyacid synthase enzyme. The monoclonal antibodies are useful to isolate and purify the enzyme. The invention also relates to peptides corresponding to fragments of the enzyme which then are used to generate the monoclonal antibodies.

BACKGROUND OF THE INVENTION

The first enzymatic step common to the biosynthesis of the branched chain amino acids (valine, leucine and isoleucine) is catalyzed by acetohydroxyacid synthase (AHAS; also known as acetolactate synthase; E.C.4.1.3.18). The enzyme catalyzes two parallel reactions: condensation of two moles of pyruvate to give rise to acetolactate, and condensation of a mole of pyruvate and a mole of α-ketobutyrate to yield acetohydroxybutyrate (Bibliography 1,2). This enzyme is inhibited by the end products of the pathway (valine, leucine and isoleucine) and this is one of the known mechanisms of regulation of this pathway in higher plants (3,4).

AHAS is the target site of four classes of structurally unrelated herbicides. These herbicides include the imidazolinones (5), the sulfonylcarboxamides (6), the sulfonylureas (7,8,9), and the triazolopyrimidines (10,11). These findings have stimulated interest in understanding why a single enzyme is inhibited by so many different classes of compounds. These findings have also suggested that there may be other classes of AHAS inhibitors which may be potentially used as herbicides, algaecides or fungicides. Due to the projected economic significance in finding such AHAS inhibitors, there is a great deal of interest in understanding the enzymology and biochemistry of this enzyme.

Three different forms of AHAS have been characterized in *Escherichia coli* and *Salmonella typhimurium*. AHAS from these enterobacteria exists as a tetramer of two large and two small subunits (12,13,14). In contrast, AHAS from plants exists in different aggregation states (15,16,17,18) which have different properties. However, it is not known whether AHAS from plants is composed of homologous or heterologous subunits. Since AHAS has been conserved across bacteria, yeast and plants (19), it has been speculated that a small subunit of AHAS may be present in plants.

Purification and characterization of eukaryotic enzyme has been severely hampered by its extreme lability and low abundance (15,20,21,22).

SUMMARY OF THE INVENTION

The significance of AHAS in plant metabolism has been established. However, difficulties in isolating the enzyme have hampered the development of AHAS inhibitors which may have utility as herbicides.

Accordingly, it is an object of this invention to develop an improved method for isolating AHAS from plants. Specifically, peptides corresponding to fragments of the amino acid sequence of AHAS are synthesized.

It is a further object of this invention to use these peptides to generate monoclonal antibodies to AHAS through the construction of novel hybridomas.

It is yet another object of this invention to generate monoclonal antibodies of sufficient specificity so that they will recognize AHAS in monocotyledonous plants, but will not recognize AHAS in dicotyledonous plants.

It is still another object of this invention to utilize the novel monoclonal antibodies to purify AHAS from plant tissue.

These objects are accomplished in the description of the invention set forth below.

BRIEF DESCRIPTION OF THE FIGURES

FIG. 1 depicts the deduced amino acid sequence of an internal region of AHAS (337 residues) from wild type corn variety W22. An "[X]" indicates that the identity of the residue is not confirmed.

DETAILED DESCRIPTION OF THE INVENTION

Figure 2:
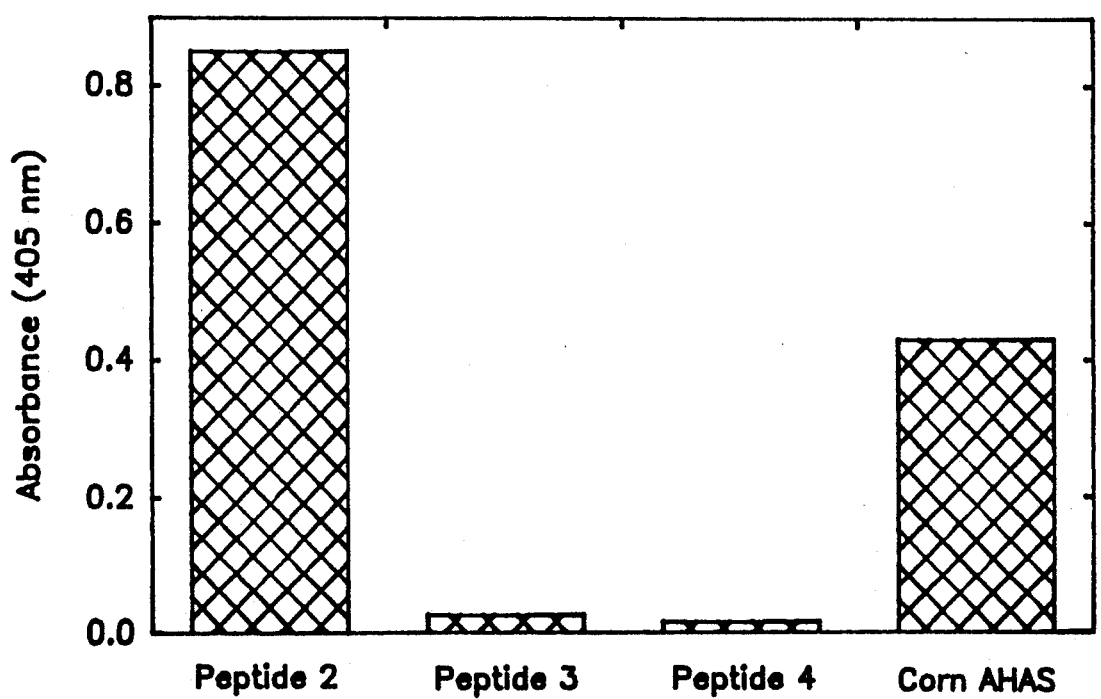
FIG. 2 depicts a study of the specificity of a monoclonal antibody designated AHAS-8 in an enzyme-linked immunosorbent assay against three peptides corresponding to portions of the deduced amino acid sequence of AHAS, and AHAS from crude corn cell extracts.

This invention is directed to the generation of monoclonal antibodies which specifically recognize AHAS in plants, in particular AHAS in monocotyledonous species.

The monoclonal antibodies are generated through the use of peptides corresponding to fragments of the amino acid sequence of AHAS. The peptides should contain from about five to about thirty amino acid residues, so as to correspond to an epitopic site or other feature of the tertiary structure of AHAS, and to which a monoclonal antibody can be generated which is specific to AHAS.

More specifically, the peptides will have primary structural homology to the amino acid sequence of a region of AHAS. A peptide having primary structural homology has the identical amino acid sequence as a specific region of the AHAS enzyme.

Alternatively, the peptides may have amino acid sequences which are antigenically equivalent to those just described. Such peptides may be said to be antigenically equivalent to peptides having amino acid sequences homologous to the corresponding portions of AHAS if their amino acid sequences differ only by minor deletions from or conservative substitutions to the AHAS sequences so that the tertiary configurations of the peptides are substantially unchanged from those of the AHAS portions and monoclonal antibodies can be generated to those peptides.

Three peptides are constructed having amino acid sequences which have primary structural homology to the corresponding portions of the AHAS enzyme from various plant species.

The DNA sequence for AHAS is known for native plant species such as arabidopsis and tobacco (19), as well as for sugarbeet (23), and putative amino acid sequences have been deduced from those DNA sequences.

A deduced partial amino acid sequence of AHAS (337 residues) from wild type corn variety W22 is shown in FIG. 1. The sequence comprises an internal region of the enzyme, rather than an amino-terminal or carboxy-terminal region. The partial amino acid sequence is deduced from cDNA which is obtained by cloning the corn variety W22 AHAS gene from a commercially available cDNA library (Clonetech, LaJolla, Calif.), and then sequencing the cDNA by conventional methods.

The amino acid sequences of the three peptides are selected by comparing the amino acid sequence deduced from the cloned corn variety W22 cDNA with the corresponding amino acid sequences deduced from the published DNA sequences of other plant AHAS genes (19,23). Peptide sequences of maximum sequence divergence (non-conserved regions) between monocot and dicot AHAS genes are identified and peptides are constructed which possess minimal amino acid sequence similarity to dicot AHAS sequences. The same strategy is employed to construct peptides which are utilized to generate monoclonal antibodies which are specific for dicots rather than monocots.

The three different peptides are designated by numbers, and their amino acid sequences (aa) and species are as follows:

| | |
|---|---|
| #2 (aa 314–328): corn | Trp-His-Asp-Glu-Leu-Asp-Gln-Gln-Asp-Arg-Glu-Phe-Pro-Leu-Gly |
| #3 (aa 247–259): corn | Arg-Phe-Asp-Asp-Arg-Val-Thr-Gly-Lys-Ile-Glu-Ala-Phe |
| #4 (aa 632–646): arabidopsis | Thr-Pro-Gly-Pro-Tyr-Leu-Leu-Asp-Val-Ile-Cys-Pro-His-Glu-Glu |

The three peptides are constructed by techniques known in the art including, but not limited to, chemical synthesis, use of a solid phase peptide synthesizer and expression by a DNA nucleotide sequence in an appropriate host.

The peptides are chosen based on the predicted immunogenicity (24), hydrophilicity (25) and secondary structure (26) in an attempt to maximize the likelihood of obtaining immune response. Even with this approach, as described below, only one cell line producing a monoclonal antibody against one of the peptides is identified.

In order to enhance the formation of monoclonal antibodies in vivo, a peptide preferably is linked to a macromolecule which functions as a carrier for the peptide. For example, the peptide may be conjugated to a protein such as keyhole limpet haemocyanin (KLH). Other carriers within the scope of this invention include those known in the art such as human and bovine serum albumins, myoglobins, $\beta$-galactosidase, penicillanase and bacterial toxoids. The carriers may also be synthetic molecules such as multi-poly-DL-ananyl-poly-L-lysine and poly-L-lysine. In a preferred embodiment of this invention, the peptides are conjugated with KLH using glutaraldehyde.

Monoclonal antibodies are prepared by immunizing mice with an AHAS peptide, removing the spleens of the mice, preparing suspensions of lymphocytes, fusing these lymphocytes to mouse myeloma cells, culturing the cells and collecting supernatants of the hybridomas which survive for antibody screening by a solid-phase enzyme-linked immunosorbent assay (ELISA). Those hybridomas which produce desired antibodies are further subcloned and are injected in mice. Ascites are then collected from the peritoneal cavities of mice and immunoglobulin G (IgG) is purified on a Protein A affinity column. Alternatively, IgG may be purified by ammonium sulfate precipitation.

Samples of IgG so purified are assayed against antigens using an ELISA to identify the antibodies formed. A monoclonal antibody designated AHAS-8 is determined to be of particular interest. Next, the immunoreactivity of monoclonal antibody AHAS-8 is examined in ELISA against three individual peptides (#2–4) which are initially used to immunize mice. It is found that the antibody reacts with peptide #2 having an amino acid sequence of Trp-His-Asp-Glu-Leu-Asp-Gln-Gln-Lys-Arg-Glu-Phe-Pro-Leu-Gly (FIG. 2). This peptide is deduced from the gene sequence for AHAS from corn. There is no significant reaction between monoclonal antibody AHAS-8 and peptides #3 and 4 (FIG. 2). In an ensuing ELISA test, a positive reaction is found between this monoclonal antibody and crude extracts from Black Mexican Sweet (BMS) corn cells (FIG. 2). Extracts from cell cultures are a good source of crude AHAS for use in assays and tests.

This specificity is further confirmed in a Western Blotting experiment where proteins in the crude extract from BMS cells are separated by sodium dodecyl sulfate-polyacrylamide gel electrophoresis (SDS-PAGE) under reducing conditions, blotted onto nitrocellulose paper and then probed with monoclonal antibody AHAS-8. Specifically, slab gel electrophoresis (11% acrylamide) is conducted by the use of a SDS-PAGE system (27). Following electrophoresis, protein is transferred to nitrocellulose sheets. The blots are developed using dilutions of the primary antibody and dilutions of goat anti-mouse IgG-alkaline phosphatase conjugate. Nitroblue tetrazolium and 5-Bromo-4-chloro-3-indolyl phosphate is used as the substrate.

Figure 3:
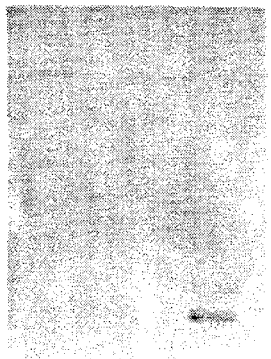
FIG. 3 depicts the detection of AHAS purified from crude extracts of Black Mexican Sweet corn cells on a Western Blot experiment. The molecular weight markers are on the right as follows: phosphorylase B (97.4 kD), bovine serum albumin (68 kD), ovalbumin (43 kD), carbonic anhydrase (29 kD), and beta-lactoglobulin (18.4 kD).

A single protein band with an apparent molecular weight of 65,000 daltons (65 kD) is detected (FIG. 3). This band is detected even at 1:300,000 dilution (20 ng IgG/gel) showing high avidity for this protein. The molecular weight of this protein matches the molecular weight of the AHAS protein sequence which is deduced from its gene sequence.

Immunoprecipation experiments unequivocally demonstrate the specificity of monoclonal antibody AHAS-8 for AHAS from BMS cells. The monoclonal antibody neutralizes the activity of AHAS.

In the experiments, the effect of monoclonal antibody AHAS-8 compared to normal IgG on AHAS activity is compared in reaction mixtures containing varying amounts of antiserum (0–100 μl). Controls for each reaction series contain either no serum or the preimmune serum. The mixtures are incubated and an aliquot is assayed for AHAS activity before and after centrifugation. The remaining sample is mixed with S. aureus cells to help in precipitation of the antigen-antibody complex. The mixture is incubated and then centrifuged. AHAS activity is measured in the supernatant and the pellet fraction. Acetolacetate formed in the tube containing no IgG or normal IgG is the same and is designated as 100% AHAS activity. Other reactions are expressed as a percentage of this activity.

Figure 4:
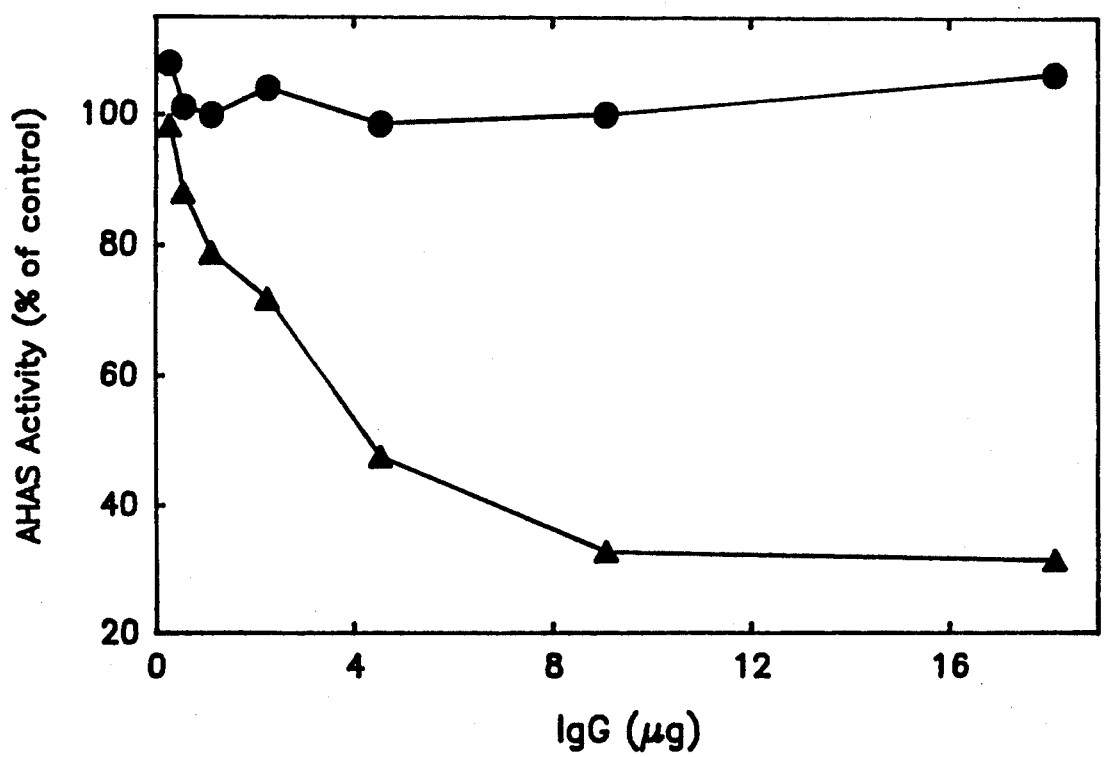
FIG. 4 depicts the neutralization by immunoprecipitation of AHAS activity by monoclonal antibody AHAS-8. The curve with solid circles depicts normal imunoglobulin. The curve with solid triangles depicts monoclonal antibody AHAS-8.

The results presented in Table 1 (see Example below) and FIG. 4 show that there is no inhibition of AHAS activity with normal IgG in any treatment. In contrast, monoclonal antibody AHAS-8 inhibits AHAS activity in the solution even without centrifugation. There is a small decrease in AHAS activity in the supernatant fraction after certrifugation. As expected, there is no AHAS activity in the pellet fraction because the enzyme activity lost from the supernatant would be expected to be present in the pellet fraction. These results suggest that monoclonal antibody AHAS-8 is binding with AHAS at the catalytic site or at a region that causes a change in the conformation of the enzyme in such a way that it is no longer enzymatically active.

Figure 5:
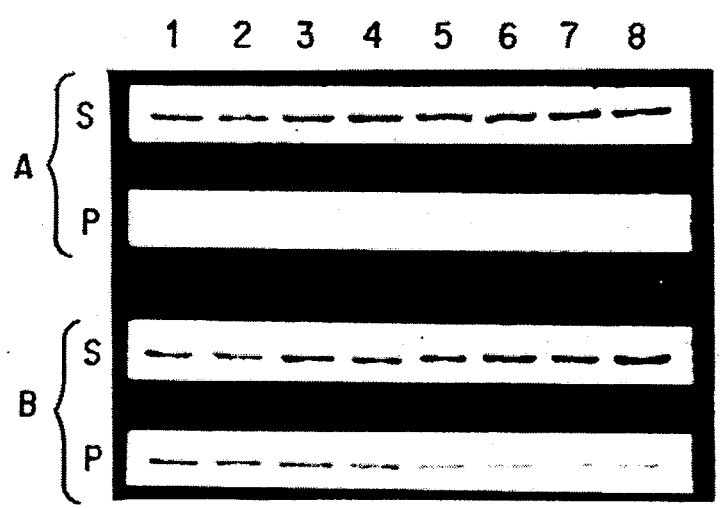
FIG. 5 depicts the detection of AHAS using monoclonal antibody AHAS-8 in the supernatant (S) and the pellet fraction (P) of a neutralization experiment (depicted in FIG. 4), followed by Western Blotting. Panel A: Normal immunoglobulin; Panel B: Monoclonal antibody AHAS-8.

The Western blots indicate there is a decreasing amount of AHAS in the supernatant fraction (comparable to the loss in AHAS activity) with increasing amounts of antibody (FIG. 5). A corresponding increase in the amount of AHAS protein in the pellet fraction is observed. No such trend with the normal IgG is observed.

Having demonstrated the specificity of the monoclonal antibody for AHAS, the monoclonal antibody is used to purify AHAS using conventional techniques. Examples of such techniques include: (1) conjugating the monoclonal antibody to an immunoaffinity column so as to bind AHAS to the monoclonal antibody, passing crude AHAS extracts through the column, and eluting the purified AHAS from the column; and (2) solubilizing the AHAS, followed by precipitation, removing the supernatant, washing the pellet which contains both antibody and antigen, passing the eluate through an immunoaffinity column to which only the antibody binds, and eluting the purified AHAS from the column.

In a preferred embodiment, an immunoaffinity column prepared by covalently conjugating monoclonal antibody AHAS-8 with a resin is used for the purification of AHAS from BMS cells. The affinity column is equilibrated and crude extracts of BMS cells (in the equilibration buffer) are passed through the column. AHAS activity is measured after passaging and the process is repeated two more times to ensure binding of AHAS to the column.

Figure 6:
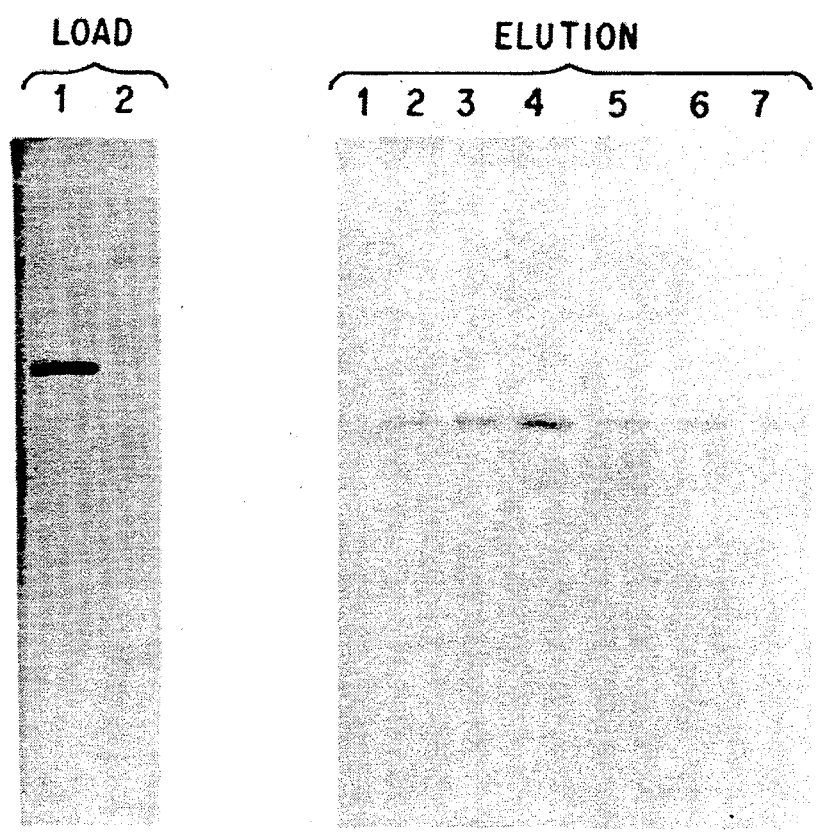
FIG. 6 depicts the immunoaffinity purification of AHAS followed by Western Blotting.

A loss of enzyme activity in the pass-through extract as compared to the crude extract indicates that the loss of enzyme activity of the pass-through extract is due to the binding of the enzyme with this resin. Unbound and non-specifically bound proteins are removed by extensively washing the column with an equilibration buffer. Specifically bound protein is eluted from the gel using an acidic buffer. Fractions are collected and neutralized with base. An aliquot from each fraction is analyzed for the presence of AHAS by Western Blot. A polypeptide with an apparent molecular weight of 65 kD is detected on the Western Blot (FIG. 6). This is identical to the result obtained in FIG. 3.

The predicted molecular weight of this protein from the gene sequence (N-terminal of the mature protein in the gene sequence determined by N-terminal sequencing of the purified protein) matches the molecular weight of the protein detected by monoclonal antibody AHAS-8 using the two procedures described above. These results provide strong evidence that AHAS in extracts of corn contains a 65 kD polypeptide.

A published report has proposed a molecular weight of 58 kD for the purified AHAS enzyme from barley based on SDS-PAGE (16). The photograph of the SDS-PAGE in that report also shows several other bands, including one in the region of 65 kD, which is not stated to represent AHAS. The band claimed to be AHAS in the work of Durner and Boger (16) may represent a breakdown product of the enzyme, or a protein other than AHAS, because, as will now be discussed, further SDS-PAGE analysis with monoclonal antibody AHAS-8 indicates that the molecular weight of AHAS from barley is in fact 65 kD, not 58 kD.

In further experiments, the cross-reaction of monoclonal antibody AHAS-8 with AHAS from different plant species is analyzed. These species include five monocots—corn (*Zea mays*), wheat (*Triticum aestivum*), barley (*Hordeum vulgare*), rice (*Oryza sativa*), and sorghum (*Sorghum bicolor*)—and seven dicots—soybean (*Glycine max*), tobacco (*Nicotiana tabacum*), spinach (*Spinacea oleracea*), arabidopsis (*Arabidopsis thaliana*), pea (*Pisum sativum*), sugarbeet (*Beta vulgaris*) and lima bean (*Phaseolus limensis*).

Figure 7:
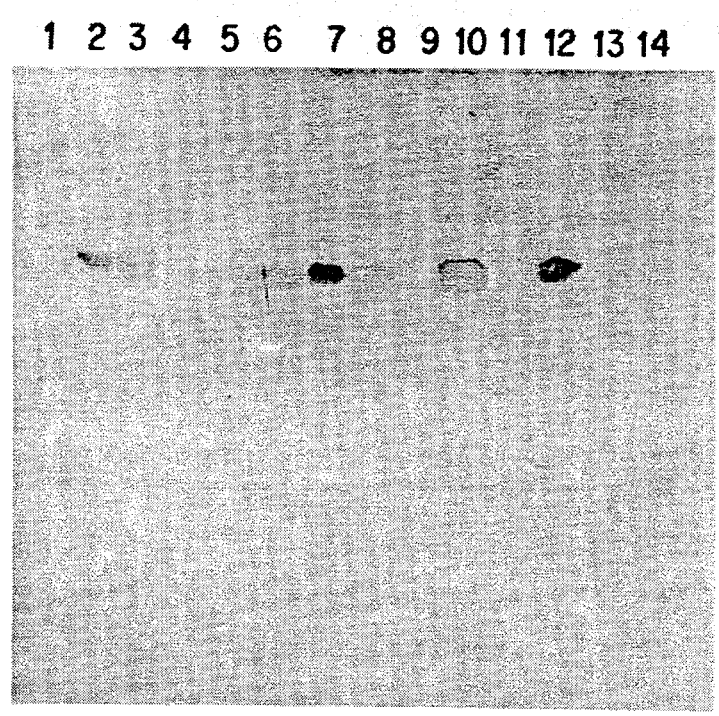
FIG. 7 depicts the cross-reaction of monoclonal antibody AHAS-8 with AHAS from various species on a Western Blot. Lanes 1 and 14 depict the molecular weight standards as follows: phosphorylase B (97.4 kD), bovine serum albumin (68 kD), ovalbumin (43 kD), carbonic anhydrase (29 kD), and beta-lactoglobulin (18.4 kD). Lanes 2-13 depict various plant species as follows: Lane 2: Black Mexican Sweet corn cells; Lane 3: sorghum; Lane 4: lima bean; Lane 5: spinach; Lane 6: barley; Lane 7: corn; Lane 8: wheat; Lane 9: pea; Lane 10: rice; Lane 11: soybean; Lane 12: Black Mexican Sweet corn cells; Lane 13: arabidopsis.

Crude extracts from each one of these species are boiled in SDS-PAGE buffer containing dithiothreitol. Western blots are developed following electrophoresis of these extracts. A protein band with an apparent molecular weight of 65 kD is detected in all monocots (FIG. 7). On the other hand, no reaction is seen with any protein band from the dicot species. The molecular weight of the protein band detected by the monoclonal antibody matches that of the predicted molecular weight of AHAS based on the gene sequence.

Even though there is a very high degree of sequence conservation (85%) between AHAS proteins from different species (19), there is only 52% or less amino acid sequence conservation between the sequence of peptide #2 from corn and the sequence of dicot species (19). Therefore, the lack of cross-reactivity of monoclonal antibody AHAS-8 with AHAS from dicot species is not suprising. Thus, monoclonal antibody AHAS-8 has a degree of specificity which makes it a powerful tool for studying the AHAS enzyme in monocots.

The lack of amino acid sequence conservation in this region is also employed to construct peptides which are utilized to generate monoclonal antibodies which react with dicot species, but not with monocot species.

This invention presents here the first demonstration of the production of a monoclonal antibody against AHAS from any source. This achievement is significant because attempts to purify this enzyme from plants have had limited success because of its low abundance and labile nature (15,16,22). The monoclonal antibodies corresponding to portions of AHAS demonstrate more specificity to AHAS than antibodies raised against the entire enzyme. Antibodies to the entire enzyme are less specific in nature and cross-react with AHAS of dicotyledonous plants. In contrast, the monoclonal antibodies to peptides are specific to monocotyledonous plant species. The novel monoclonal antibodies may be used in efforts to develop varieties of AHAS which are resistant to herbicides.

In order that this invention may be better understood, the following example is set forth. The example is for the purpose of illustration only and is not to be construed as limiting the scope of the invention.

EXAMPLE

1. Preparation of AHAS Peptides

Three different peptides corresponding to portions of the AHAS enzyme from corn and arabidopsis are chemically synthesized using a Biosearch 9600 (Miligen Biosearch, Burlington, Mass.) solid phase peptide synthesizer according to the protocol provided by the manufacturer.

The three different peptides are designated by numbers, and their amino acid sequences (aa) and species are as follows:

| | |
|---|---|
| #2 (aa 314-14 328): corn | Trp-His-Asp-Glu-Leu-Asp-Gln-Gln-Asp-Arg-Glu-Phe-Pro-Leu-Gly |
| #3 (aa 247-14 259): corn | Arg-Phe-Asp-Asp-Arg-Val-Thr-Gly-Lys-Ile-Glu-Ala-Phe |
| #4 (aa 632-14 646): arabidopsis | Thr-Pro-Gly-Pro-Tyr-Leu-Leu-Asp-Val-Ile-Cys-Pro-His-Glu-Glu |

The purity of the peptides is confirmed by analytical HPLC. The peptides are lyophilized and stored at −20° C. in a dessicator cabinet until used.

2. Conjugation of AHAS Peptides with KLH

Each of the three peptides from step 1 of this Example is dissolved in phosphate buffered saline (PBS) (Gibco, Grand Island, N.Y.) and mixed with KLH (Sigma Chemical Co., St. Louis, Mo.) at an approximate molar ratio of 25 to 1. Glutaraldehyde (0.5%) is added as a coupling agent and each mixture is incubated at room temperatures for 15 to 60 minutes. NaBH$_4$ is subsequently added and each conjugation mixture is dialyzed extensively against PBS. The aggregates are removed by high speed centrifugation (10,000 g) and each concentration is determined by a UV spectrophotometer at a wavelength of 280 nm.

3 Generation of Monoclonal Antibody AHAS-8

Balb/C mice, six to ten weeks of age, are purchased from Charles River Breeding Laboratories, Wilmington, Mass. These mice are separated into three groups. Each group is immunized with 100 μg of a KLH-peptide conjugate in the presence of complete Freund's adjuvant. Three booster injections with 50 μg of the same anitgen are given every three weeks thereafter. Their spleens are removed three days after the last booster immunization and single cell suspensions of lymphocytes are prepared. These lymphocytes are fused with SP2/0 mouse myeloma cells lacking hypoxanthine phosphoribosyl transferase (HPRT) with 50% polyethylene glycol, suspended in Dulbecco's modified Eagle medium (D-MEM) containing 20% fetal calf serum (Gibco), 0.175 μg/ml aminopterin, 13.6 μg/ml hypoxanthine, 3.88 μg/ml thymidine and 50 μg/ml gentamicin (HAT medium), and finally dispensed in 96-well culture plates. After being cultured for 10–14 days, supernatants of the approximately 80 hybridomas which survive due to the HPRT-positive phenotype of the lymphocytes are collected for antibody screening in an ELISA. The only hybridoma found to produce appropriate antibodies (by consistently achieving high titers in supernatants) is further subcloned by a limited dilution procedure to produce antibodies of interest.

The hybridoma designated AHAS-8 produces a monoclonal antibody of interest, which is designated MoAb AHAS-8. Samples of the hybridoma AHAS-8 have been deposited with the American Type Culture Collection (ATCC) 12301 Parklawn Drive, Rockville, Md. 20852 U.S.A. and have been assigned accession number HB 10484. The hybridoma AHAS-8 was deposited on Jun. 21, 1990. The selected positive clone is injected intraperitoneally into Balb/C mice which are primed with pristane for the production of antibody-containing ascites.

4. Preparation of Monoclonal Antibody

Ascites are collected from the peritoneal cavities of mice and IgG is purified by diluting ascites fluid to 50% with binding buffer (3M NaCl, 1.5M glycine, pH 8.9) and loading onto a Protein A Sepharose CL-4B column (Pharmacia, Piscataway, N.J.). The non-IgG fraction is eluted from the column with the binding buffer and the bound IgG is subsequently eluted with 0.1M citric acid, pH 3. It is immediately neutralized to pH 8.9 with 1.5M Tris buffer, pH 8.9. The monoclonal antibody so prepared is concentrated by ultrafiltration (Amicon, Danvers, Mass.), extensively dialyzed against phosphate-buffered saline (PBS), aliquoted, and finally stored at −70° C. until use.

5. Solid Phase ELISA

The immunoreactivity of the monoclonal antibody against AHAS (designated AHAS-8) is examined in an ELISA against individual peptides (#2-4) which are initially used to immunize mice. Antigens are dissolved in PBS and 1 μg in 100 μl is added to each well of a 96-well flat bottom polystyrene plate. After being incubated for one hour, the plate is washed three times with PBS containing 0.05% Tween-20 by an automatic plate washer (Dynatech Wash II, Chantilly, Va.). Each well is dispensed with 200 μl of 2% bovine serum albumin (BSA) and the plate is incubated for another hour. Test samples are added to the wells, incubated for 30 minutes, washed six times with PBS, and added with 100 μl of alkaline phosphatase-conjugated goat anti-mouse IgG F(ab')$_2$ (Zymed Laboratories, South San Francisco, Calif.). The plate is again washed after a 30 minute incubation and 100 μl of p-nitrophenyl phosphate (1 mg/ml, Sigma, St. Louis, Mo.) in 0.1M diethanolamine, pH 10.3, is added as substrate for color development. Finally, the colorimetric response is recorded as optical density (OD) by an ELISA plate reader at a wavelength of 405 nm. All incubations are performed at 37° C.

It is found that the antibody reacts with peptide #2 having an amino acid sequence of Trp-His-Asp-Glu-Leu-Asp-Gln-Gln-Lys-Arg-Glu-Phe-Pro-Leu-Gly (FIG. 2). This peptide corresponds to residues 314–328 of the amino acid sequence deduced from the gene sequence for AHAS from corn.

The specificity of monoclonal antibody AHAS-8 is then further examined in an ELISA test against AHAS from corn. Embryo-derived cell suspension cultures of Zea mays variety Black Mexican Sweet (BMS), are obtained from Molecular Genetics (Minnetonka, Minn., U.S.A.) and cultured on Murashige and Skoog salts (28,29) with 2% (W/V) sucrose, 500 mg/l thiamine, 2 mg/l (2,4-dichlorophenoxy)acetic acid with 150 mg/l asparagine with shaking at 100 rpm in the dark at 22° C. Cells are harvested on day 7 by filtration through a nylon cloth, washed with deionized water and squeezed to remove excess water.

In an ensuing ELISA test, a positive reaction with this monoclonal antibody AHAS-8 to AHAS from crude BMS cell extracts is found (FIG. 2). There is no significant reaction between monoclonal antibody AHAS-8 and peptides #3 and 4 (FIG. 2).

6 Western Blotting

These findings of step 5 are further confirmed in a Western Blotting experiment where AHAS from crude plant and cell extracts is separated by SDS-PAGE under reducing conditions, blotted onto nitrocellulose paper and then probed with monoclonal antibody AHAS-8.

Plant material is prepared from green seedlings of the following species: corn (*Zea mays*), wheat (*Triticum aestivum*), barley (*Hordeum vulgare*), rice (*Oryza sativa*), sorghum (*Sorghum bicolor*), soybean (*Glycine max*), tobacco (*Nicotiana tabacum*), spinach (*Spinacea oleracea*), arabidopsis (*Arabidopsis thaliana*), pea (*Pisum sativum*), sugarbeet (*Beta vulgaris*) and lima bean (*Phaseolus limensis*). Seeds are planted in soil and grown in a greenhouse. Shoots or leaves from one week old seedlings are used for the extraction of the enzyme.

AHAS is extracted from the plant material just described and the corn cells from step 5 as follows: The plant material or cells are powdered in liquid nitrogen and then homogenized in 100 mM potassium phosphate buffer (pH 7.5) containing 10 mM pyruvate, 5 mM magnesium chloride, 5 mM EDTA, 100 $\mu$M flavin adenine dinucleotide (FAD), 1 mM valine, 1 mM leucine, 10% (v/v) glycerol and 10 mM cysteine. The homogenate is filtered through a nylon cloth (53 $\mu$M mesh) and centrifuged at 25,000 g for 20 minutes. The supernatant fraction is brought to 50% saturation with respect to ammonium sulfate and allowed to stand for 20–30 minutes on ice. It is then centrifuged at 25,000 g for 20 minutes and the supernatant is discarded. The ammonium sulfate pellet is used immediately or frozen with liquid nitrogen and then stored at −20° C. until used.

To confirm the presence of AHAS in the pellet fraction, a Western Blotting experiment is conducted where samples from each of the treatments described above are subjected to slab gel electrophoresis (11% acrylamide) using a SDS-PAGE system (27). Following electrophoresis, protein is transferred to nitrocellulose sheets and probed with monoclonal antibody AHAS-8 using the protocol provided by the manufacturer (Bio Rad, Richmond, Calif.). The blots are developed using 1:1000 dilution of the primary antibody, 1:1500 dilution of goat anti-mouse IgG-alkaline phosphatase conjugate, and Nitroblue tetrazolium and 5-Bromo-4-chloro-3-indolyl phosphate, as substrate according to the protocol provided by Bio Rad.

A single protein in the crude extracts of corn with an apparent molecular weight of 65 kD is identified by SDS-PAGE followed by Western blotting and immunological detection (FIG. 3). This band is detected even at 1:300,000 dilution (20 ng IgG/gel) showing high avidity for this protein.

The molecular weight of this protein matches the molecular weight of the AHAS protein sequence which is deduced from its gene sequence. These results along with the data from immunoprecipation experiments (described below) unequivocally demonstrate the specificity of monoclonal antibody AHAS-8 for AHAS from BMS cells.

7. Neutralization of AHAS Activity with Monoclonal Antibody

The effect of antisera (normal IgG and monoclonal antibody AHAS-8) on AHAS activity is then determined. The ammonium sulfate pellet collected from prior extraction steps is dissolved in 50 mM phosphate (pH 7), 150 mM NaCl and 10 $\mu$M FAD, then desalted on a bed of pre-packed Sephadex G-25 column according to the manufacturer's protocol (Bio Rad, Richmond, Calif.). The buffer used for dissolving ammonium sulfate pellets is also used for the equilibration of the column and elution of AHAS from this column.

To establish a baseline, the activity of purified AHAS is ascertained by estimation of the product, acetolactate, after conversion by acid decarboxylation to acetoin (30). Thereafter, standard reaction mixtures are prepared containing the purified AHAS enzyme in 50 mM potassium phosphate buffer (pH 7.0) containing 100 mM sodium pyruvate, 10 mM magnesium chloride, 1 mM thiamine pyrophosphate (TPP) and 10 $\mu$M FAD. This mixture is incubated at 37° C. for 1 hour. The reaction is stopped with the addition of sulfuric acid to make a final concentration of 0.85%. The reaction product is allowed to decarboxylate at 60° C. for 15 minutes. The acetoin formed is determined by incubating with creatine (0.17%) and 1-naphthol (1.7%) by the method of Westerfield (31). Appropriate checks of direct acetoin formation during the enzyme assay are made. Protein concentrations are determined by the Bradford method (32) according to the protocol supplied by the manufacturer (Bio Rad, Richmond, Calif.).

Test reaction mixtures containing 50 mM phosphate buffer, pH 7.0, 150 mM NaCl, 10 $\mu$M FAD, desalted AHAS enzyme and varying amounts of antiserum (0–100 $\mu$l) are then prepared. Controls for each reaction series contain either no serum or the preimmune serum. After incubation at room temperature for 30 minutes, the mixtures are further incubated on ice for 2 hours. Following incubation, an aliquot is taken and assayed for AHAS activity before and after centrifugation 10,000 g for 5 minutes. The mixture is incubated for 30 minutes at 4° C. and then centrifuged. AHAS activity is measured in the supernatant and the pellet fraction. Acetolacetate formed in the tube containing no IgG or normal IgG is the same and is designated as 100% AHAS activity. Other reactions are expressed as a percentage of this activity.

Results presented in Table 1 and FIG. 4 show that there is no inhibition of AHAS activity with normal IgG in either treatment (average of all data presented):

TABLE 1

Effect of antibody on AHAS activity in the supernatant fraction

| Immunoglobulin | Centrifugation | Relative Activity |
|---|---|---|
| Normal | No | 100 |
| Normal | Yes | 100 |
| AHAS-8 | No | 50 |

TABLE 1-continued

| Effect of antibody on AHAS activity in the supernatant fraction | | |
|---|---|---|
| Immunoglobulin | Centrifugation | Relative Activity |
| AHAS-8 | Yes | 45 |

On the other hand, monoclonal antibody AHAS-8 is able to inhibit AHAS activity in the solution itself, even without centrifugation. There is a small decrease in AHAS activity in the supernatant fraction after centrifugation.

This conclusion concerning the inhibitory activity is also supported by the fact that there is no AHAS activity in the pellet fraction (as the enzyme activity lost from the supernatant would be expected to be present in the pellet fraction).

As expected, there is a decreasing amount of AHAS in the supernatant fraction (comparable to the loss in AHAS activity) with increasing amounts of antibody (FIG. 5). A corresponding increase in the amount of AHAS protein in the pellet fraction is observed. No such trend with the normal IgG is observed.

8. Immunoaffinity Purification of AHAS

An immunoaffinity column is prepared by covalently conjugating purified monoclonal antibody AHAS-8 to an amino-link antigen/antibody purification resin (Pierce, Rockford, Ill.) according to the manufacturer's protocol. The column is used to purify AHAS from BMS cells. About 2.5 mg of IgG is covalently bound to 2 ml of resin. The affinity column is equilibrated with 50 mM potassium phosphate (pH 7), 150 mM NaCl and 10 $\mu$M FAD, and then 200 ml of crude extracts of BMS cells (in the equilibration buffer) are passed through the column four times. AHAS activity is measured after each passage. After four passages, there is a 50% loss of the enzyme activity as compared to the enzyme which is kept on ice for that time period. This result indicates that the loss of enzyme activity from the extract passed through the affinity resin is due to the binding of the enzyme with this resin. The column is then washed with 50 ml of equilibration buffer (25 bed volume) to remove the unbound and non-specifically bound proteins (as measured by the lack of any UV absorbance). Elution of the bound protein is carried out with 100 mM citrate buffer (pH 3). Fractions (1 ml) are collected in tubes containing 0.3 ml of 1.5M tris-HCl (pH 8.9) to immediately neutralize the solution. An aliquot from each fraction is analyzed for the presence of AHAS by Western Blot.

When specifically bound protein is eluted from the gel using a low pH buffer, a polypeptide with an apparent molecular mass of 65 kD is detected on the Western Blot (FIG. 6). The predicted molecular weight of this protein from the gene sequence (N-terminal of the mature protein in the gene sequence determined by N-terminal sequencing of the purified protein) matches the molecular weight of the protein detected by monoclonal antibody AHAS-8. These results provide strong evidence that AHAS in extracts of corn contains a 65 kD polypeptide.

9. Cross-Reaction of Monoclonal Antibody AHAS-8 with AHAS from Different Species Monoclonal antibody AHAS-8 is used to test for cross-reaction with AHAS from different species. These species include five monocots (corn, wheat, rice, barley and sorghum) and five dicots (soybean, lima bean, pea, spinach, and arabidopsis). Crude extracts from each one of these species are boiled in SDS-PAGE buffer containing 2 mM dithiothreitol. Western blots are developed following electrophoresis of these extracts. A protein band with an apparent molecular weight of 65 kD is detected in all monocots (FIG. 7, lanes 2,3,6,7,8,10,12). On the other hand, no reaction is seen with any protein band from the dicot species (FIG. 7, lanes 4,5,9,11,13). The molecular weight of the protein band detected by the monoclonal antibody matches the predicted molecular weight of AHAS based on the gene sequence. Similar results are obtained when the experiment is repeated with two other dicots (tobacco and sugarbeet).

BIBLIOGRAPHY

1. Umbarger, H. E., *Ann. Rev. Biochem.*, 38, 323-370 (1969).
2. Umbarger, H. E., in *Escherichia coli* and *Salmonella typhimurium:* Cellular and Molecular Biology. ASM, Washington, D.C. (eds. Neidhardt, F. C., Ingraham, J. L., et al), 352-367 (1987).
3. Miflin, B. J., *Arch. Biochem. Biophys.*, 146, 542-550 (1971).
4. Miflin, B. J., and Cave, P. R., *J. Exp. Botany*, 23, 511-516 (1972).
5. Shaner, D. L., et al., *Plant Physiol.*, 76, 545-546 (1984).
6. Crews, A. D., et al., *Abstr. Pap. Am. Chem. Soc.*, 198, Meet. Agro. No. 39.
7. Chaleff, R. S., and Mauvais, C. J., *Science*, 224, 1443-1445 (1984).
8. La Rossa, R. A., and Schloss, J. V., *J. Biol Chem.*, 259, 8753-8757 (1984).
9. Ray, T. B., *Plant Physiol.*, 75, 827-831 (1984).
10. Kleswick, W. A., et al., Eur. Patent appl. 0142152 (1984).
11. Subramanian, M. V., et al., pages 97-100, in "Prospects for Amino Acid Biosynthesis Inhibitors in Crop Protection and Pharmaceutical Chemistry", (eds. Coping, L. G., et al.) (1989).
12. Eoyant, L., and Silverman, P. M., *J. Bacteriol.*, 157, 184-89 (1984).
13. Grimminger, H., and Umbarger, H. E., *Journal of Bacteriology*, 137, 846-853 (1979).
14. Schloss, J. V., et al., *Biochemistry*, 24, 4952-4859 (1985).
15. Muhitch, M. J., et al., *Plant Physiol.*, 83, 451-456 (1987).
16. Durner, J., and Boger, P., *Z. Naturforsch.*, 43c, 850-856 (1988).
17. Singh, B. K., and Schmitt, G. K., *FEBS Letts.*, 258, 113-115 (1989).
18. Durner, J., and Boger, P., pages 85-86, in "Prospects for Amino Acid Biosynthesis Inhibitors in Crop Protection and Pharmaceutical Chemistry", (eds. Coping, L. G., et al.) (1989).
19. Mazur, B. J., et al., *Plant Physiol.* 85, 1110-1117 (1987).
20. Magee, P. T., and DeRobichon-Szulmajster, H., *Eur. J. Biochem.*, 3, 507-511 (1968).
21. Takenaka, S., and Kuwana, H., *J. Biochem.*, 72, 1139-1145 (1972).
22. Wittenback, V. A., and Erbes, D. L., *Plant Physiol.*, 80S, 66 (1986).
23. European patent application number 257,993.
24. Hopp, T. P., and Woods, K. R., *Proc. Nat. Acad. Sci.*, 78, 3824-3828 (1981).

25. Kyte, J., and Doolittle, R. F., *J. Mol. Biol.*, 157, 105–132 (1982).
26. Chou, P., and Fashman, G. D., *Adv. Enzymol.*, 47, 45–147 (1987).
27. Neville, D. M., *J. Biol. Chem.*, 246, 6328–6334 (1971).
28. Anderson, P. C., and Hibberd, K. A., *Weed Sci.*, 33, 479–83 (1985).
29. Murashige, T., and Skoog, F., *Physiol. Plant.*, 15, 473–497 (1962).
30. Singh, B. K., et al., *Anal. Biochem.*, 171, 173–179 (1988).
31. Westerfield, W. W., *J. Biol. Chem.*, 161, 495–502 (1945).
32. Bradford, M. M., *Anal. Biochem.*, 72, 248–254 (1976).

We claim:

1. A monoclonal antibody produced by immunization with a peptide having the amino acid sequence Trp-His-Asp-Glu-Leu-Asp-Gln-Gln-Asp-Arg-Glu-Phe-Pro-Leu-Gly, wherein said monoclonal antibody specifically binds to Acetohydroxyacid Synthase (AHAS) produced by monocotyledonous plants.

2. A monoclonal antibody according to claim 1 wherein said monoclonal antibody is that designated monoclonal antibody AHAS-8 which is produced by the hybridoma deposited with the ATCC under the accession number HB 10484.

3. A hybridoma designated AHAS-8 which is deposited with the ATCC under the accession number HB 10484.